United States Patent
van Laak et al.

(10) Patent No.: US 6,528,651 B1
(45) Date of Patent: Mar. 4, 2003

(54) METHOD FOR PRODUCTION OF 1,3-DISUBTITUTED 2-NITROGUANIDINES

(75) Inventors: Kai van Laak, Köln (DE); Wolfram Sirges, Düsseldorf (DE); Detlef Wollweber, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/149,891

(22) PCT Filed: Dec. 8, 2000

(86) PCT No.: PCT/EP00/12495

§ 371 (c)(1),
(2), (4) Date: Jun. 14, 2002

(87) PCT Pub. No.: WO01/46160

PCT Pub. Date: Jun. 28, 2001

(30) Foreign Application Priority Data

Dec. 21, 1999 (DE) .......................... 199 61 604

(51) Int. Cl.$^7$ ............................................. C07D 213/02
(52) U.S. Cl. ...................... 546/332; 548/205; 549/495
(58) Field of Search ................... 546/332; 548/205; 549/495

(56) References Cited

U.S. PATENT DOCUMENTS

| | | | |
|---|---|---|---|
| 5,034,404 A | 7/1991 | Uneme et al. | 514/365 |
| 5,051,434 A | 9/1991 | Kozo et al. | 514/357 |
| 5,084,467 A | 1/1992 | Shiokawa et al. | 514/357 |
| 5,204,359 A | 4/1993 | Shiokawa et al. | 514/332 |
| 5,238,949 A | 8/1993 | Shiokawa et al. | 514/327 |
| 5,489,603 A | 2/1996 | Uneme et al. | 514/365 |
| 5,633,375 A | 5/1997 | Uneme et al. | 544/336 |
| RE35,811 E | 5/1998 | Shiokawa et al. | 514/357 |
| 6,187,773 B1 | 2/2001 | Wu et al. | 514/245 |
| 6,194,575 B1 | 2/2001 | Wollweber et al. | 544/180 |
| 2001/0046994 A1 | 11/2001 | Wu et al. | 514/241 |

FOREIGN PATENT DOCUMENTS

| | | |
|---|---|---|
| CA | 2052731 | 4/1992 |
| EP | 0 483 062 | 4/1992 |
| EP | 0 386 565 | 1/1994 |
| EP | 0 375 907 | 1/1996 |
| EP | 869120 A1 * | 3/1998 |
| JP | 3-291267 | 12/1991 |
| JP | 10-67766 | 3/1998 |
| WO | 99/09009 | 2/1999 |

OTHER PUBLICATIONS

**Patent Abstracts of Japan, vol. 1998, No. 11, Sep. 30, 1998 & JP 10 147580 A (Mitsui Chem Inc), Jun. 2, 1998 Zusammenfassung.

* cited by examiner

*Primary Examiner*—Zinna Northington Davis
(74) *Attorney, Agent, or Firm*—Joseph C. Gil; Raymond J. Harmuth

(57) ABSTRACT

The present invention relates to a process for the preparation of compounds of the formula (I)

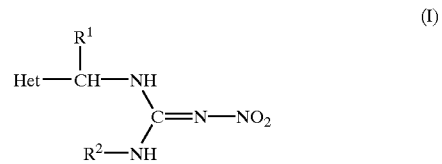

by reacting compounds of the formula (II)

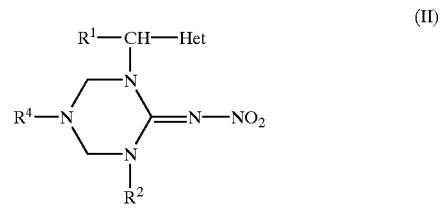

in which

Het, $R^1$, $R^2$ and $R^4$ are as defined in the description, with anhydrous hydrogen chloride or compounds which generate hydrogen chloride.

1 Claim, No Drawings

METHOD FOR PRODUCTION OF 1,3-DISUBTITUTED 2-NITROGUANIDINES

This application is a 371 of PCT/EP00/12495 filed Dec. 8, 2000.

The present invention relates to a novel type of process for the preparation of 1,3-disubstituted 2-nitroguanidines.

EP-A-0 483 062 discloses a process for the preparation of 1,3-disubstituted 2-nitroguanidines. They are obtained by hydrolysis of corresponding 2-nitroimino-1,3,5-triazacyclohexane derivatives. The hydrolysis is preferably carried out in the presence of strong mineral acids or organic acids.

Disadvantages of this process are the long reaction times and the formation of secondary products, which make it necessary to subject the desired end-products to a complex cleaning operation.

Moreover, as is known, when working in the presence of aqueous, strong acids, costly measures must be taken to protect, for example, the reactors, from corrosion.

Applications JP 03 291 267, JP 10067766 and JP 10147580 relate to similar processes.

The object of the present invention was to provide an improved process for the preparation of 1,3-disubstituted 2-nitroguanidines.

The present invention provides a process for the preparation of compounds of the formula (I)

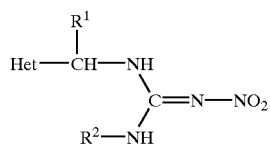

in which $R^1$ is hydrogen or alkyl, $R^2$ is hydrogen, alkyl, cycloalkyl or —$CH_2R^3$, $R^3$ is alkenyl, alkinyl, or aryl or heteroaryl, each of which is optionally substituted, Het is an unsubstituted or substituted aromatic or non-aromatic, monocyclic or bicyclic heterocyclic radical, preferably from the series

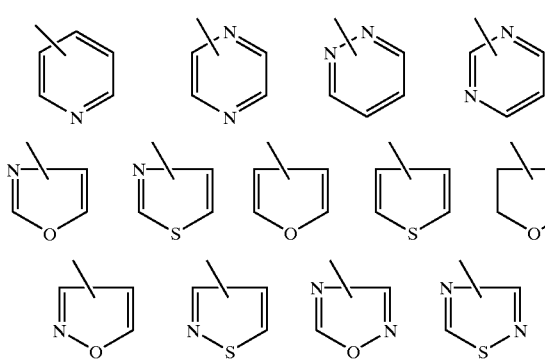

characterized in that a compound of the formula (II)

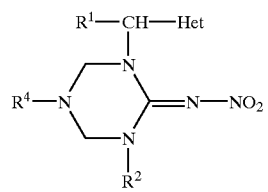

in which $R^1$, $R^2$ and Het are as defined above, and $R^4$ is alkyl, cycloalkyl, aryl, arylalkyl or heterocyclylalkyl, each of which may be unsubstituted or substituted, is reacted with anhydrous hydrogen chloride or with one or more compounds which can generate hydrogen chloride in the presence or absence of a diluent.

The compounds of the formula (I) can also be in the form of double-bond isomers as regards the —N=C(2) bond and in their tautomeric forms (formulae Ia, Ib):

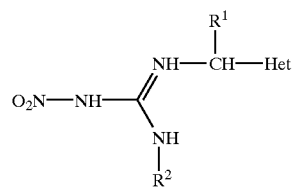

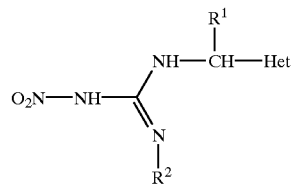

Formula (I) is accordingly to be taken to mean that it also includes the corresponding double-bond isomers and the formulae (Ia) and (Ib).

Surprisingly, the process according to the invention produces, selectively and in high yields, the end-products of the formula (I) in pure form after a short reaction time under mild reaction conditions.

For example, using 1-(2-chlorothiazol-5-ylmethyl)-2-nitro-imino-5-benzyl-3-methyl-1,3,5-triazacyclohexane as starting material, the course of the process according to the invention can be shown by the following equation:

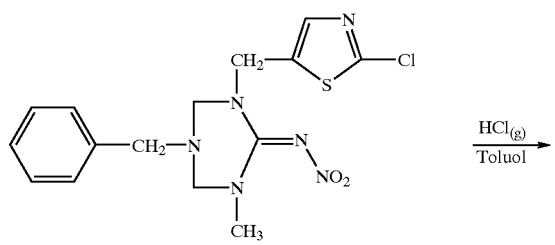

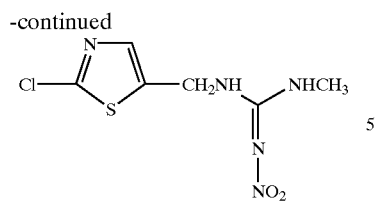

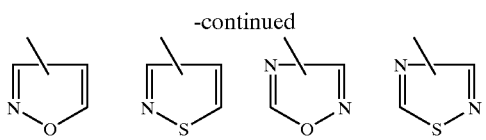

which, also depending on the type of heterocycle, can contain one or two substituents from the group consisting of $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_2$–$C_3$-halogenoalkenyl having from 1 to 4 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy, halogenoallylthio, cyano, nitro, $C_1$–$C_3$-alkyl, $C_1$–$C_3$-alkoxy and halogen.

The compounds required as starting materials for the process according to the invention are generally defined by the formula (II).

Preferred substituents and ranges of the radicals listed in the formulae mentioned above and below are illustrated below:

$R^1$ is preferably hydrogen or $C_1$–$C_4$-alkyl, $R^2$ is preferably hydrogen, $C_1$–$C_6$-alkyl, $C_3$–$C_6$-cycloalkyl or —$CH_2R^3$, $R^3$ is preferably $C_2$–$C_5$-alkenyl, $C_2$–$C_5$-alkinyl, phenyl, cyanophenyl, nitrophenyl, halogenophenyl having from 1 to 3 halogen atoms, phenyl substituted by $C_1$–$C_3$alkyl, $C_1$–$C_3$halogenoalkyl having from 1 to 7 halogen atoms, $C_1$–$C_3$-alkoxy or $C_1$–$C_3$-halogenoalkoxy having from 1 to 7 halogen atoms, 3-pyridyl, 5-thiazolyl, 5-thiazolyl substituted by one to two (preferably one) substituents from the group consisting of $C_1$–$C_3$-alkyl, $C_1$–$C_3$-halogenoalkyl having from 1 to 7 halogen atoms, cyclopropyl, halogenocyclopropyl, $C_2$–$C_3$-alkenyl, $C_2$–$C_3$-alkinyl, $C_1$–$C_3$-alkoxy, $C_2$–$C_3$-halogenoalkenyl having from 1 to 4 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy, halogenoallylthio, halogen, cyano and nitro; or 3-pyridyl substituted by one to four (preferably one) radicals from the group consisting of $C_1$–$C_3$-halogenoalkyl having from 1 to 7 halogen atoms, cyclopropyl, halogenocyclopropyl, $C_2$–$C_3$-alkenyl, $C_2$–$C_3$-alkinyl, $C_2$–$C_3$-halogenoalkenyl having from 1 to 4 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy, halogenoallylthio, cyano, nitro, $C_1$–$C_3$-alkyl, $C_{1-C3}$-alkoxy and halogen, Het is preferably an unsubstituted or substituted aromatic or nonaromatic, monocyclic or bicyclic heterocyclic radical, preferably from the series

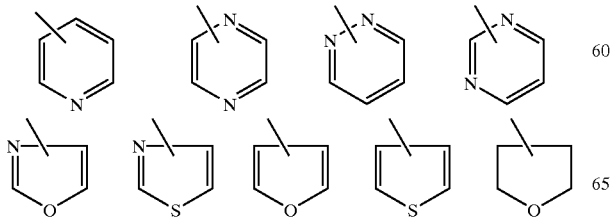

$R^4$ is preferably $C_1$–$C_{10}$-alkyl, $C_3$–$C_6$-cycloalkyl, $C_1$–$C_{10}$-alkyl substituted by from 1 to 6 radicals from the group consisting of halogen, hydroxyl, $C_1$–$C_4$-alkoxy, $C_1$–$C_4$-halogenoalkoxy having from 1 to 9 halogen atoms, di-($C_1$–$C_4$-alkyl)-amino and $C_1$–$C_5$-alkoxycarbonyl, $C_3$–$C_6$-cycloalkyl substituted by from 1 to 4 radicals from the series $C_1$–$C_4$-alkyl and halogen, phenyl, benzyl, or phenyl or benzyl substituted by from 1 to 3 ring substituents from the group consisting of halogen, $C_1$–$C_4$-alkyl, $C_1$–$C_4$-halogenoalkyl having from 1 to 9 halogen atoms, $C_1$–$C_4$-alkoxy, $C_1$–$C_4$-halogenoalkoxy having from 1 to 9 halogen atoms, $C_1$–$C_4$-alkylthio, nitro or cyano, or heterocyclylmethyl where heterocyclyl is an unsaturated or saturated 5- or 6-membered heterocycle having one or two (preferably one) heteroatoms from the series nitrogen, oxygen and sulphur (in particular furyl, tetrahydrofuryl, thienyl or pyridyl).

$R^1$ is particularly preferably hydrogen, methyl, ethyl, n- or i-propyl, $R^2$ is particularly preferably hydrogen, methyl, ethyl, n-propyl, i-propyl or n-butyl, cyclopropyl, cyclopentyl, cyclohexyl or —$CH_2R^3$, $R^3$ is particularly preferably $C_2$–$C_5$-alkenyl, $C_2$–$C_5$-alkinyl, phenyl, cyanophenyl, nitrophenyl, halogenophenyl having from 1 to 3 halogen atoms, phenyl substituted by $C_1$–$C_3$-alkyl, $C_1$–$C_3$-halogenoalkyl having from 1 to 7 halogen atoms, $C_1$–$C_3$-alkoxy or $C_1$–$C_3$-halogenoalkoxy having from 1 to 7 halogen atoms, 3-pyridyl, 5-thiazolyl, or 5-thiazolyl substituted by one or two (preferably one) substituents from the group consisting of $C_1$–$C_3$-alkyl, $C_1$–$C_3$-halogenoalkyl having from 1 to 7 halogen atoms, cyclopropyl, halogenocyclopropyl, $C_2$–$C_3$-alkenyl, $C_2$–$C_3$-alkinyl, $C_1$–$C_3$-alkoxy, $C_2$–$C_3$-halogenoalkenyl having from 1 to 4 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy, halogenoallylthio, halogen, cyano or nitro; or 3-pyridyl substituted by one to two (preferably one) radicals from the group consisting of $C_1$–$C_3$-halogenoalkyl having from 1 to 7 halogen atoms, cyclopropyl, halogenocyclopropyl, $C_2$–$C_3$-alkenyl, $C_2$–$C_3$-alkinyl, $C_2$–$C_3$-halogenoalkenyl having from 1 to 4 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy, halogenoallylthio, cyano, nitro, $C_1$–$C_3$-alkyl, $C_1$–$C_3$-alkoxy or halogen.

Het is particularly preferably an unsubstituted or mono- or disubstituted (preferably monosubstituted) heterocyclic radical from the series

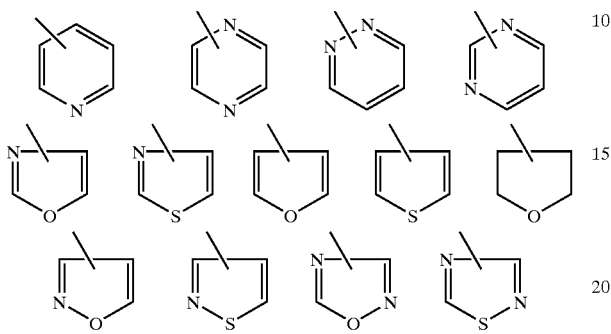

in particular from the series

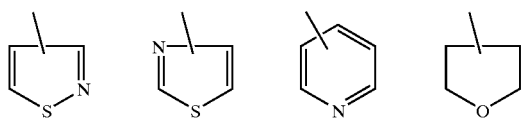

where the substituents are chosen from the series fluorine, chlorine, bromine, methyl, ethyl, methoxy and ethoxy.

$R^4$ is particularly preferably $C_1$–$C_4$-alkyl optionally substituted by halogen (in particular fluorine or chlorine), or $C_3$–$C_6$-cycloalkyl, phenyl, phenyl-$C_1$–$C_4$-alkyl or heterocyclylmethyl, each of which may be substituted by halogen (in particular fluorine or chlorine) or $C_1$–$C_4$-alkyl, where heterocyclyl [lacuna] an unsaturated or saturated 5- or 6-membered heterocycle having one or more heteroatoms from the series nitrogen, oxygen and sulphur (in particular thienyl, pyridyl, furyl or tetrahydrofuryl).

$R^1$ is very particularly preferably hydrogen, methyl or ethyl, $R^2$ is very particularly preferably hydrogen, methyl, ethyl, n-propyl, i-propyl, n-butyl, cyclopropyl, cyclopentyl, cyclohexyl or a radical —$CH_2R^3$, $R^3$ is very particularly preferably $C_2$–$C_3$-alkenyl, $C_2$–$C_3$-alkinyl, phenyl, cyanophenyl, nitrophenyl, halogenophenyl having from 1 to 3 halogen atoms, phenyl substituted by $C_1$–$C_3$-alkyl, $C_1$–$C_3$-halogenoalkyl having from 1 to 7 halogen atoms, $C_1$–$C_3$-alkoxy or $C_1$–$C_3$-halogenoalkoxy having from 1 to 7 halogen atoms, 3-pyridyl, 5-thiazolyl, 5-thiazoyl or 3-pyridyl substituted in each case by one or two (preferably one) substituents from the group consisting of $C_1$–$C_3$-alkyl, $C_1$–$C_3$-halogenoalkyl having from 1 to 7 halogen atoms, $C_1$–$C_3$-alkoxy, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, halogen, cyano or nitro, $R^4$ is very particularly preferably $C_1$–$C_4$-alkyl, cyclopropyl, cyclopentyl or cyclohexyl $C_1$–$C_4$-alkyl substituted by halogen, $C_3$–$C_6$-cycloalkyl substituted in each case by 1 or 2 radicals from the series methyl, ethyl, fluorine and chlorine, is phenyl, benzyl or phenyl, benzyl, furylmethyl, tetrahydrofurylmethyl, thienylmethyl or pyridylmethyl in each case substituted by 1 or 2 ring substituents from the group consisting of methyl, ethyl, fluorine and chlorine.

Het is very particularly preferably thiazolyl, pyridyl or tetrahydrofuranyl, each of which may be unsubstituted or mono- or disubstituted (in particular monosubstituted), the substituents being chosen from the series fluorine, chlorine, methyl and methoxy.

In the definitions, unless stated otherwise, halogen (atoms) is F, Cl, Br, I, preferably F, Cl, Br, particularly preferably F, Cl.

$R^1$ is very particularly preferably hydrogen, methyl or ethyl, especially hydrogen, $R^2$ is very particularly preferably hydrogen, methyl, ethyl, n-propyl, cyclopropyl, cyclopentyl, allyl, propargyl or p-chlorobenzyl, especially methyl.

$R^4$ is very particularly preferably methyl, ethyl, n-propyl, cyclopropyl, cyclopentyl, cyclohexyl, phenyl, benzyl or tetrahydrofurylmethyl, Het is very particularly preferably one of the radicals

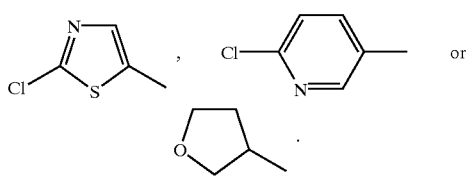

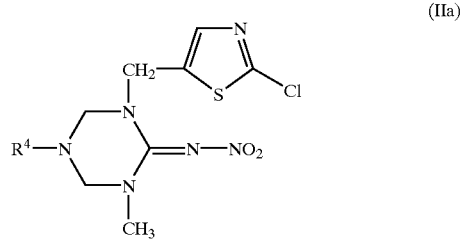

Particularly preferred starting materials for the process according to the invention are compounds of the formula (IIa)

(IIa)

in which $R^4$ is methyl, ethyl, cyclopropyl, cyclopentyl, benzyl or tetrahydrofurylmethyl, where, of these, methyl, benzyl and tetrahydrofurylmethyl are in turn preferred.

Particularly preferred starting materials for the process according to the invention are compounds of the formula (IIb) and (IIc)

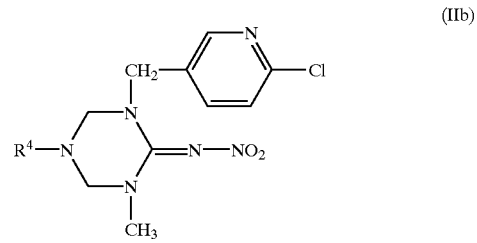

(IIb)

-continued

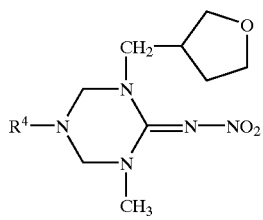
(IIc)

in which

R⁴ is as defined for the compounds of the formula (IIa).

The end-products of the process according to the invention are, when the compound of the formula (IIa) is used, the following compound

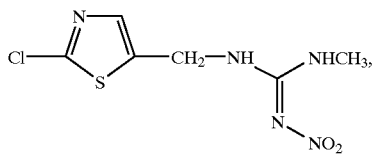

when the compound of the formula (IIb) is used, the following compound

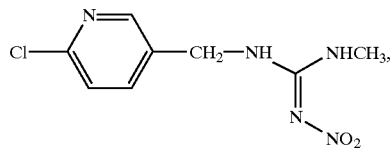

and when the compound of the formula (IIc) is used, the following compound

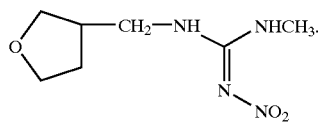

The radical definitions and explanations given in general terms above or listed in the preferred ranges can be combined with one another as desired, i.e. also between the respective ranges and preferred ranges. They apply to the end-products and also to the precursors and intermediates.

The term alkyl also means here the branched isomers, e.g. t-butyl for $C_4$-alkyl.

Preference is given to using those compounds of the formula (II) which have a combination of the preferred meanings given above in the process according to the invention.

Particular preference is given to using those compounds of the formula (II) which have a combination of the particularly preferred meanings given above in the process according to the invention.

Very particular preference is given to using those compounds of the formula (II) which have a combination of the very particularly preferred meanings given above in the process according to the invention.

The starting materials of the formula (II) are known or can be prepared by known processes (cf. EP-A-0 483 062, JP-03 291 267, EP-A-0 483 055, EP-A-0 428 941, EP-A-0 386 565, WO 98/42690).

The process according to the invention is carried out by reacting the compounds of the formula (II) with anhydrous hydrogen chloride or with compounds which are able to generate hydrogen chloride with protic solvents, in particular with alcohols or carboxylic acids.

The compounds which can generate hydrogen chloride include, for example, acid chlorides in particular compounds of the formula (III) (Group A):

(III)

in which

R⁵ alkyl, cycloalkyl, aryl, arylalkyl or heterocyclylalkyl, each of which may be substituted.

R⁵ is preferably $C_1$–$C_{10}$-alkyl, $C_3$–$C_{10}$-cycloalkyl, aryl-$C_1$–$C_4$-alkyl, in particular phenyl-$C_1$–$C_4$-alkyl, each of which may be mono- or polysubstituted, where suitable substituents are OH, SH, halogen, $C_1$–$C_6$-alkoxy, $C_1$–$C_6$-alkylthio, $C_1$–$C_6$-alkyl and aryl, in particular phenyl, or is heterocyclylmethyl, where heterocyclyl is an unsaturated or saturated 5- or 6-membered heterocycle having one or two (preferably one) heteroatoms from the series nitrogen, oxygen, sulphur, in particular furyl, tetrahydrofuryl, thienyl or pyridyl.

Here, halogen (atoms) is preferably F, Cl, Br, I, in particular F, Cl, Br and especially F, Cl.

R⁵ is particularly preferably $C_1$–$C_4$-alkyl, $C_3$–$C_6$-cycloalkyl, benzyl or phenylethyl, each of which may be monosubstituted to pentasubstituted (preferably monosubstituted to trisubstituted, particularly preferably monosubstituted or disubstituted), where suitable substituents are OH, Cl, Br, F, $C_1$–$C_4$-alkoxy, $C_1$–$C_4$-alkylthio, $C_1$–$C_4$-alkyl and aryl, in particular phenyl; or heterocyclylmethyl, where heterocyclyl is, in particular furyl, tetrahydrofuryl, thienyl or pyridyl.

R⁵ is very particularly preferably the respective radical R⁴ of the compound of the formula (II) to be reacted or one of the radicals from the series benzyl, HO—CH₂—CH₂—, n-hexyl or cyclohexyl.

The compounds of the formula (III) are known and are available commercially or can be readily prepared by known methods.

The compounds which are able to generate hydrogen chloride also include (Group B):

reactive nonmetal and metal chlorides, and also reactive nonmetal and metal oxychlorides, preferably boron trichloride, aluminium trichloride, silicon tetrachloride, oxalyl chloride, trichlorosilane, phosphorus trichloride, phosphorus pentachloride, phosphorus oxychloride, sulphur dichloride, titanium tetrachloride, titanium trichloride, vanadium trichloride, vanadium(V) oxytrichloride, thionyl chloride and sulphuryl chloride, particularly preferably aluminium chloride, phosphorus trichloride, phosphorus pentachloride, phosphorus oxychloride, thionyl chloride, sulphuryl chloride and oxalyl chloride, very particularly preferably thionyl chloride, sulphuryl chloride, phosphorus oxychloride and oxalyl chloride.

The compounds of group B are known compounds which are available commercially as such or can be prepared in a known manner.

The process according to the invention is optionally carried out in the presence of a diluent.

Suitable diluents when using hydrogen chloride are organic solvents, polar protic [lacuna], such as methanol, ethanol, n-propanol, i-propanol, n-butanol or i-butanol, and also polar aprotic solvents, for example acetone, acetonitrile and acetic ester (e.g. ethyl acetate), ethers and cyclic ethers, such as diethyl ether, diisobutyl ether, THF, dioxane, or nonpolar, aprotic solvents, such as hydrocarbons, for example benzene, toluene or xylene, halogenated hydrocarbons, such as methylene chloride, chloroform, tetrachloromethane, chlorobenzene or o-dichlorobenzene.

It is also possible to use mixtures of said diluents.

Suitable diluents when using compounds of group (A) or (B) are polar, protic solvents, for example alcohols or carboxylic acids.

Particularly suitable are alcohols, in particular methanol, ethanol, n-propanol, i-propanol, n-butanol, i-butanol.

It may be advantageous to add another diluent to the reaction mixture. Suitable solvents are ethers, for example dibutyl ether, THF, dioxane, glycoldimethylether or diglycoldimethylether, and also hydrocarbons, such as benzene, toluene or xylene, halogenated hydrocarbons, such as methylene chloride, chloroform, tetrachloromethane, chlorobenzene or o-dichlorobenzene, nitriles, such as acetonitrile, carboxylic esters, such as ethyl acetate or also ketones, such as acetone or methyl isopropyl ketone.

Mixtures of said diluents may also be used.

The process according to the invention is generally carried out at temperatures between 0° C. and 200° C., preferably between 40° C. and 150° C.

The process is preferably carried out under atmospheric pressure and, particularly in the case of low-boiling diluents, it can optionally also be carried out under increased pressure.

The anhydrous hydrogen chloride and the compounds of the formula (III) or of group B are generally used in a molar ratio of from 0.5:1 to 10:1, preferably 1:1 to 5:1, based on the starting compound of the formula (II).

The reaction is generally carried out by heating the starting material of the formula (II), and the hydrogen chloride or the compound of the formula (III) or (IV), optionally in a diluent and optionally in a solvent, to the desired temperature. It is also possible to meter in successively the hydrogen chloride or the compound of the formula (III) or of group B over the course of the reaction.

To work-up, after cooling, water is optionally added, and the end-product, optionally after evaporating the mixture, is isolated, for example by filtration or extraction.

The reaction is preferably carried out in a diluent from which, when the reaction mixture is cooled, the end product can be directly crystallized out and isolated in a simple manner, for example by filtration. Suitable diluents for this purpose are alcohols, in particular methanol, ethanol, propanol, i-propanol, isobutanol, n-butanol, sec-butanol.

It is also possible to work up the reaction mixture without water by, when the reaction is complete, distilling off the diluent where appropriate and the solvent where appropriate and extracting the residue which remains with a suitable extractant. Suitable extractants are, in principle, all solvents which are inert with respect to the end-products and in which the end-products are sufficiently soluble.

Examples thereof include aliphatic hydrocarbons, such as n-pentane, n-hexane, cyclohexane, halogenated aliphatic hydrocarbons, such as methylene chloride or chloroform, aromatic hydrocarbons, such as benzene, toluene or xylene, halogenated aromatic hydrocarbons, such as chlorobenzene or o-dichlorobenzene or else ethers, such as, for example, methyl tert-butyl ether.

The end-products crystallize out, optionally after evaporating off the extractant, and can be isolated by filtration, or the extractant is completely or virtually completely removed and, if necessary, the residue is purified, for example by recrystallization.

The compounds of the formula (I) prepared according to the invention are useful active ingredients in pest control. In particular, the compounds of the formula (I) are suitable for controlling insects and arachnids, which are encountered in useful and ornamental plants in agriculture, in particular, cotton, vegetable and fruit plantations, in forests, in the protection of stored products and materials and in the hygiene sector, in particular on pets and useful animals (see e.g. EP-A-0 376 279, EP-A-0 375 907, EP-A-0 383 091).

EXAMPLES

Example 1

Preparation of 1-(2-chlorothiazol-5-ylmethyl)-2-nitro-3-methylguanidine

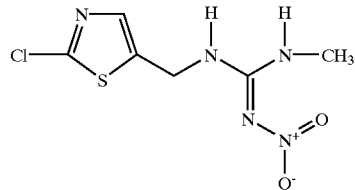

a) 19.2 g of 1-(2-chlorothiazol-ylmethyl)-2-nitro-imino-5-benzyl-3-methyl-1,3,5-triazacyclohexane

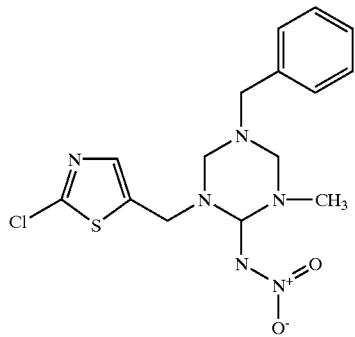

are dissolved in 100 ml of anhydrous toluene, and, at 65° C., dry HCl gas is introduced. The mixture is then stirred for five hours at 65° C. and the product is isolated by filtration. The crystals are then dried.

Yield: 16.2 g, purity (HPLC): 75%, selectivity: 99%

The crude product is stirred with 50 ml of butanol at 50° C., and the solid is filtered off at 25° C. and dried.

Yield: 10.5 g, purity (HPLC): 98%

According to its chromatographic and spectroscopic data, the product is identical to an authentic sample of 1-(2-chlorothiazol-5-ylmethyl)-2-nitro-3-methylguanidine obtained by another route.

b) 19.2 g of 1-(2-chlorothiazol-5-ylmethyl)-2-nitro-imino-5-benzyl-3-methyl-1,3,5-triazacyclohexane are dissolved in 100 ml of anhydrous acetone, and, at 20° C., dry HCl gas is introduced. The mixture is then stirred for five hours at 20° C. and the product is isolated by filtration. The crystals are then dried.

Yield: 19.8 g, purity (HPLC): 62%, selectivity: 99% c) 19.2 g of 1-(2-chlorothiazol-5-ylmethyl)-2-nitro-imino-5-benzyl-3-methyl-1,3,5-triazacyclohexane are dissolved in 100 ml of anhydrous ethyl acetate, and, at 65° C., dry HCl gas is introduced. The mixture is then stirred for five hours at 65° C. and the product is isolated by filtration. The crystals are then dried.

Yield: 16.5 g, purity (HPLC): 75%, selectivity: 99% d) 19.2 g of 1-(2-chlorothiazol-5-ylmethyl)-2-nitro-imino-5-benzyl-3-methyl-1,3,5-triazacyclohexane are dissolved in 100 ml of anhydrous methanol, and, at 20° C., dry HCl gas is introduced. The mixture is then stirred for one hour at 20° C. and the product is isolated by filtration. The crystals are then dried.

Yield: 14.2 g, purity (HPLC): 79%, selectivity: 91% e) 19.2 g of 1-(2-chlorothiazol-5-ylmethyl)-2-nitro-imino-5-benzyl-3-methyl-1,3,5-triazacyclohexane are dissolved in 100 ml of anhydrous methanol. At 40° C., 5.1 g of acetyl chloride are added dropwise over 20 minutes, and the mixture is then stirred for three and a half hours at 40° C. The resulting suspension is cooled to 0–5° C. and the product is isolated by filtration. The crystals are then dried.

Yield: 11.1 g, purity (HPLC): 99% f) 19.2 g of 1-(2-chlorothiazol-5-ylmethyl)-2-nitro-imino-5-benzyl-3-methyl-1,3,5-triazacyclohexane are dissolved in 100 ml of anhydrous methanol. At 25° C., 7.7 g of thionyl chloride are added dropwise over 15 min, and the mixture is then stirred for three hours at this temperature. The resulting suspension is cooled to 0–5° C. and the product is isolated by filtration. The crystals are then dried.

Yield 10.8 g, purity (HPLC): 98% g) 19.2 g of 1-(2-chlorothiazol-5-ylmethyl)-2-nitro-imino-5-benzyl-3-methyl-1,3,5-triazacyclohexane are dissolved in 100 ml of anhydrous methanol. At 25° C., 8.3 g of oxalyl chloride are added dropwise over 25 min, and the mixture is then stirred for five hours at 40° C. The resulting suspension is cooled to 0–5° C. and the product is isolated by filtration. The crystals are then dried.

Yield 10.4 g, purity (HPLC): 98% h) 19.2 g of 1-(2-chlorothiazol-5-ylmethyl)-2-nitro-imino-5-benzyl-3-methyl-1,3,5-triazacyclohexane are dissolved in 100 ml of anhydrous methanol. At 25° C., 6.3 g of methyl chloroformate are added dropwise over 10 min, and the mixture is then stirred for five hours at 40° C. The resulting suspension is cooled to 0–5° C. and the product is isolated by filtration. The crystals are then dried.

Yield 10.9 g, purity (HPLC): 98% i) 19.2 g of 1-(2-chlorothiazol-5-ylmethyl)-2-nitro-imino-5-benzyl-3-methyl-1,3,5-triazacyclohexane are dissolved in 100 ml of anhydrous methanol. At 25° C., 7.3 g of chloroacetyl chloride are added dropwise over 10 min, and the mixture is then stirred for five hours at 40° C. The resulting suspension is cooled to 0–5° C. and the product is isolated by filtration. The crystals are then dried.

Yield 10.9 g, purity (HPLC): 98% j) 19.2 g of 1-(2-chlorothiazol-5-ylmethyl)-2-nitro-imino-5-benzyl-3-methyl-1,3,5-triazacyclohexane are dissolved in 100 ml of anhydrous methanol. At 25° C., 10 g of phosphorus oxychloride are added dropwise over 30 min, and the mixture is then stirred for one hour at 40° C. The resulting suspension is cooled to 0–5° C. and the product is isolated by filtration. The crystals are then dried.

Yield: 9.1 g, purity: 97.1%

Using a similar method, it is also possible to obtain the compounds of the formula (I) given in the table below:

TABLE

| Example No. | Het | $R^1$ | $R^2$ |
|---|---|---|---|
| 2 | 2-chloropyridin-5-yl | H | H |
| 3 | 2-chloropyridin-5-yl | H | —$CH_3$ |
| 4 | 2-chloropyridin-5-yl | H | —$C_2H_5$ |
| 5 | 2-chloropyridin-5-yl | H | —$C_3H_7(n)$ |
| 6 | 2-chloropyridin-5-yl | H | cyclopropyl |
| 7 | 2-chloropyridin-5-yl | H | —$C_4H_9(n)$ |
| 8 | 2-chloropyridin-5-yl | H | —$CH(CH_3)_2$ |
| 9 | 2-chloropyridin-5-yl | H | —$CH_2$—phenyl |
| 10 | 2-chloropyridin-5-yl | H | —$CH_2$-(pyridin-3-yl) |
| 11 | 2-chloropyridin-5-yl | H | —$CH_2$-(2-chloropyridin-5-yl) |
| 12 | 2-chloropyridin-5-yl | H | —$CH_2$-(4-chlorophenyl) |
| 13 | 2-chloropyridin-5-yl | —$CH_3$ | —$CH_3$ |

TABLE-continued

| Example No. | Het | R¹ | R² |
|---|---|---|---|
| 14 | 6-chloropyridin-3-yl | —CH₃ | —C₂H₅ |
| 15 | 6-chloropyridin-3-yl | —CH₃ | cyclopropyl |
| 16 | 6-chloropyridin-3-yl | —CH₃ | —C₃H₇(n) |
| 17 | 6-chloropyridin-3-yl | —C₂H₅ | —CH₃ |
| 18 | 6-chloropyridin-3-yl | —C₂H₅ | —C₂H₅ |
| 19 | 6-chloropyridin-3-yl | —C₂H₅ | cyclopropyl |
| 20 | 2-chlorothiazol-5-yl | H | H |
| 21 | 2-chlorothiazol-5-yl | H | CH₃ |
| 22 | 2-chlorothiazol-5-yl | H | —C₂H₅ |
| 23 | 2-chlorothiazol-5-yl | H | cyclopropyl |
| 24 | 2-chlorothiazol-5-yl | H | —CH₂—C₆H₅ |
| 25 | 2-chlorothiazol-5-yl | H | —CH₂—C₆H₄—Cl |
| 26 | 2-chlorothiazol-4-yl | CH₃ | CH₃ |
| 27 | 2-chlorothiazol-4-yl | C₂H₅ | CH₃ |
| 28 | 2-chlorothiazol-4-yl | CH₃ | C₂H₅ |
| 29 | 2-chlorothiazol-4-yl | CH₃ | cyclopropyl |
| 30 | 6-chloropyridin-3-yl | H | —CH₂—CH=CH₂ |
| 31 | 6-chloropyridin-3-yl | H | —CH₂—C≡CH |
| 32 | 2-chloro-5-methylthiazol-4-yl | H | —CH₂—CH=CH₂ |
| 33 | 2-chloro-5-methylthiazol-4-yl | H | —CH₂—C≡CH |
| 34 | 4-methyltetrahydrofuran-3-yl | H | CH₃ |
| 35 | 4-methyltetrahydrofuran-3-yl | CH₃ | CH₃ |

What is claimed is:

1. A process for the preparation of a compound of the Formula (I)

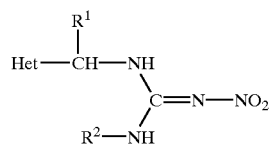 (I)

wherein
- $R^1$ is hydrogen or alkyl,
- $R^2$ is hydrogen, alkyl, cycloalkyl or —$CH_2R^3$,
- $R^3$ is alkenyl, alkinyl, or aryl or heteroaryl each of which is optionally substituted,
- Het is an unsubstituted or substituted aromatic or non-aromatic, monocyclic or bicyclic heterocyclic radical, comprising the step of:

reacting a compound of the formula (II)

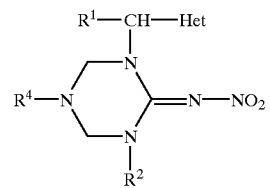 (II)

wherein
- $R^1$, $R^2$ and Het are as defined above, and
- $R^4$ is alkyl, cycloalkyl, aryl, arylalkyl or heterocyclylalkyl, each of which may be unsubstituted or substituted, with anhydrous hydrogen chloride or with one or more compounds which can generate hydrogen chloride in the presence or absence of a diluent.

* * * * *